United States Patent
Franklin, Jr.

(10) Patent No.: US 6,939,333 B1
(45) Date of Patent: Sep. 6, 2005

(54) COMBINATION TAMPON/PANTY SHIELD

(76) Inventor: Wilbur Franklin, Jr., P.O. Box 18852, Irvine, CA (US) 92623-8852

(*) Notice: Subject to any disclaimer, the term of this patent is extended or adjusted under 35 U.S.C. 154(b) by 0 days.

(21) Appl. No.: 10/043,610

(22) Filed: Jan. 9, 2002

(51) Int. Cl.[7] ............................................. A61F 13/20
(52) U.S. Cl. .............. 604/385.17; 604/11; 604/385.13
(58) Field of Search ............................ 604/363, 385.17, 604/385.18, 385.19, 904, 385.13, 11

(56) References Cited

U.S. PATENT DOCUMENTS

| | | | | |
|---|---|---|---|---|
| 3,604,423 A | * | 9/1971 | Fraser | 604/385.13 |
| 3,865,110 A | * | 2/1975 | Traverse | 604/365 |
| 4,027,673 A | * | 6/1977 | Poncy et al. | 604/369 |
| 4,380,450 A | * | 4/1983 | Reich | 604/386 |
| 4,857,066 A | * | 8/1989 | Allison | 604/385.13 |
| 5,141,505 A | * | 8/1992 | Barrett | 604/385.13 |
| 5,389,181 A | * | 2/1995 | Vukos et al. | 156/264 |
| 5,702,379 A | * | 12/1997 | Preiss | 604/385.11 |
| 6,059,763 A | * | 5/2000 | Brown | 604/385.17 |
| 6,186,995 B1 | * | 2/2001 | Tharpe, Jr. | 604/385.18 |
| 2002/0068894 A1 | * | 6/2002 | Wada et al. | 604/15 |

* cited by examiner

Primary Examiner—John J. Calvert
Assistant Examiner—Linh Truong

(57) ABSTRACT

A combination tampon/panty shield that is inserted and removed without the need for the user's hands or fingers contacting the vagina. The combination tampon/panty shield includes a panty shield portion including the moisture proof outer layer provided with two exterior pockets and a centrally located finger insertion cavity extending inward through an in inner absorbent layer adhesively bonded to a backside of the moisture proof outer layer and a tampon extending upward from the inner absorbent layer and having a portion of the finger insertion cavity extending into a bottom tampon portion thereof.

1 Claim, 3 Drawing Sheets

COMBINATION TAMPON/PANTY SHIELD

TECHNICAL FIELD

The present invention relates to feminine hygiene products and more particularly to a combination tampon/panty shield that includes a panty shield portion including a moisture proof outer layer provided with two exterior pockets and a centrally located finger insertion cavity extending inward through an in inner absorbent layer adhesively bonded to a backside of the moisture proof outer layer and a tampon extending upward from the inner absorbent layer and having a portion of the finger insertion cavity extending into a bottom tampon portion thereof; the two exterior pockets and the finger insertion cavity being used during insertion and/or removal of the tampon into or out of the vagina.

BACKGROUND

Putting in and taking out a tampon can easily spread contamination between the user's hands and fingers to the user's vagina where infections and the like can result. It would be a benefit, therefore, to have a combination tampon/panty shield that could be inserted and removed without the need for the user's hands or fingers contacting the vagina.

GENERAL SUMMARY DISCUSSION OF INVENTION

It is thus an object of the invention to provide a combination tampon/panty shield that includes a panty shield portion including a moisture proof outer layer provided with two exterior pockets and a centrally located finger insertion cavity extending inward through an in inner absorbent layer adhesively bonded to a backside of the moisture proof outer layer and a tampon extending upward from the inner absorbent layer and having a portion of the finger insertion cavity extending into a bottom tampon portion thereof; the two exterior pockets and the finger insertion cavity being used during insertion and/or removal of the tampon into or out of the vagina.

Accordingly, a combination tampon/panty shield is provided. The combination tampon/panty shield includes a panty shield portion including a moisture proof outer layer provided with two exterior pockets and a centrally located finger insertion cavity extending inward through an in inner absorbent layer adhesively bonded to a backside of the moisture proof outer layer and a tampon extending upward from the inner absorbent layer and having a portion of the finger insertion cavity extending into a bottom tampon portion thereof; the two exterior pockets and the finger insertion cavity being used during insertion and/or removal of the tampon into or out of the vagina.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein.

EXEMPLARY MODE FOR CARRYING OUT THE INVENTION

Figure 1:
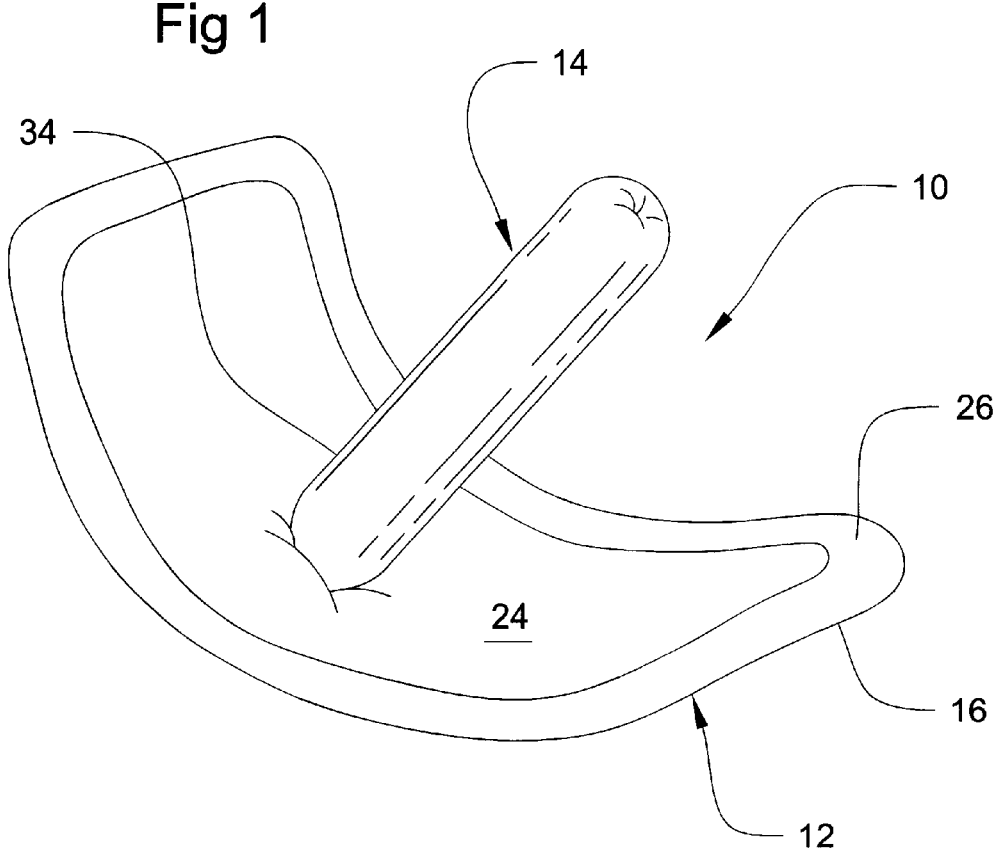
FIG. 1 is a perspective view of an exemplary embodiment of the combination tampon/panty shield of the present invention showing the panty shield portion and the tampon.
Figure 2:
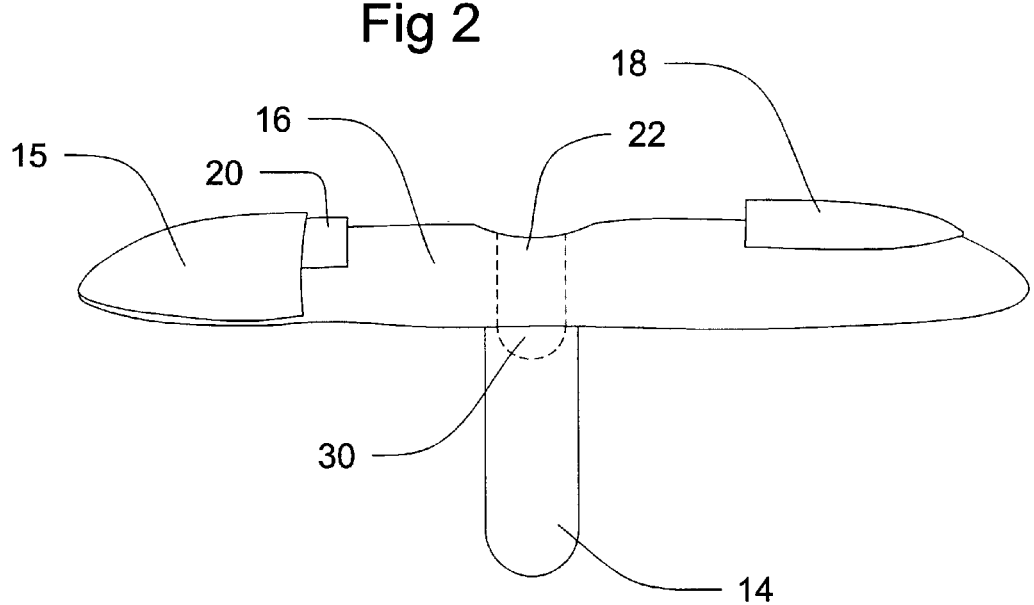
FIG. 2 is side plan view of the combination tampon/panty shield showing the panty shield portion including the moisture proof outer layer provided with two exterior pockets and a centrally located finger insertion cavity extending inward through an in inner absorbent layer adhesively bonded to a backside of the moisture proof outer layer and the tampon extending upward from the inner absorbent layer and having a portion of the finger insertion cavity extending into a bottom tampon portion thereof.
Figure 3:
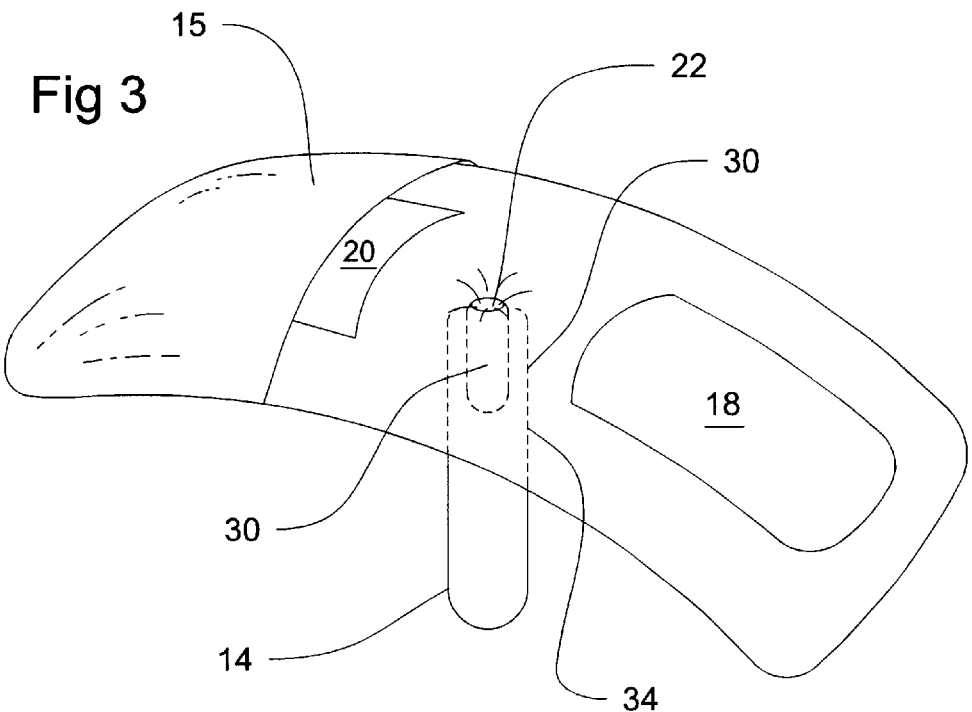
FIG. 3 is a perspective view of the combination tampon/panty shield.
Figure 4:
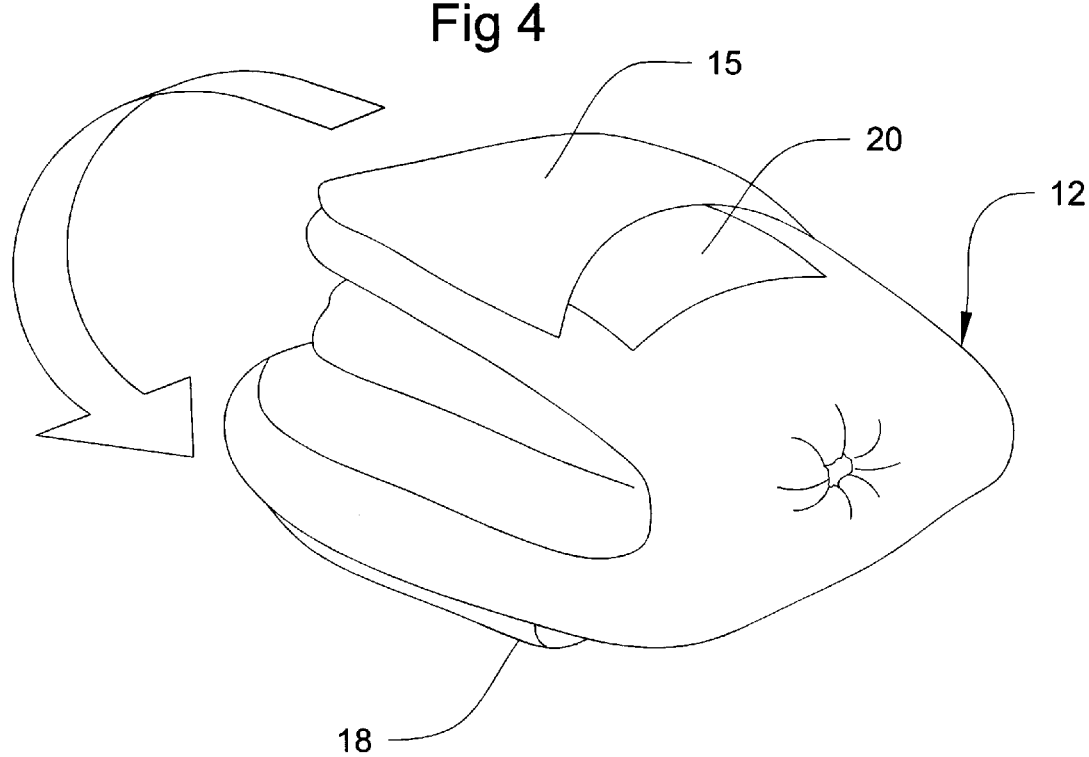
FIG. 4 is a perspective view of the combination tampon/panty shield folded prior to inserting it into the provided disposal pouch.
Figure 5:
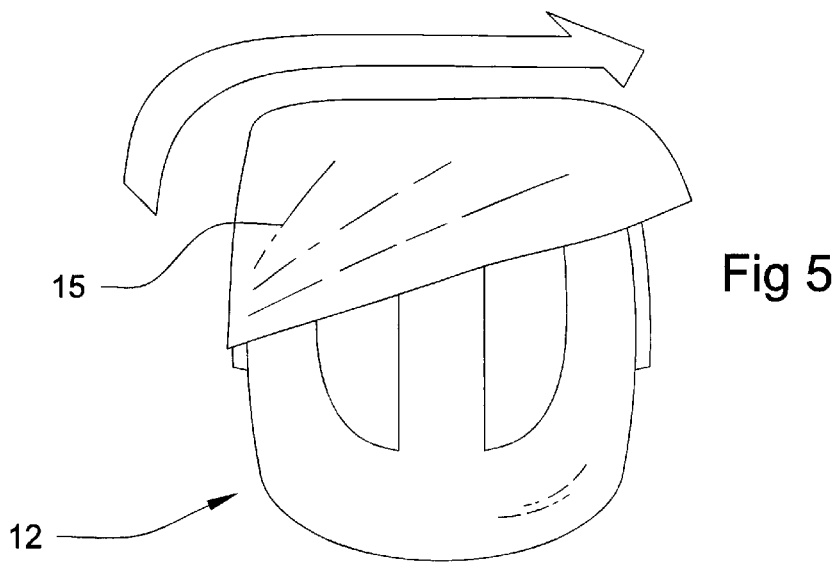
FIG. 5 is a plan view of the combination tampon/panty shield with the disposal pouch partially covering the combination panty shield/tampon.
Figure 6:
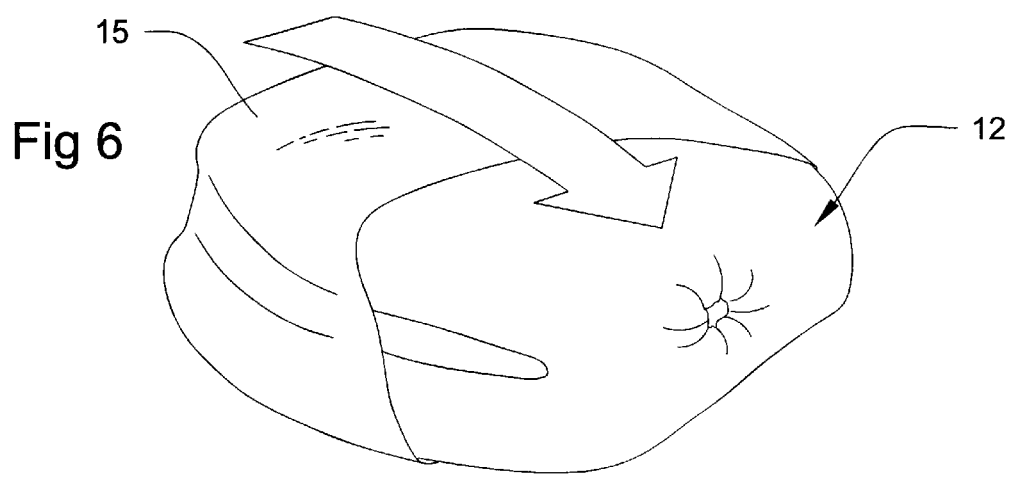
FIG. 6 is a perspective view of the combination tampon/panty shield partially inserted into the disposal pouch
Figure 7:
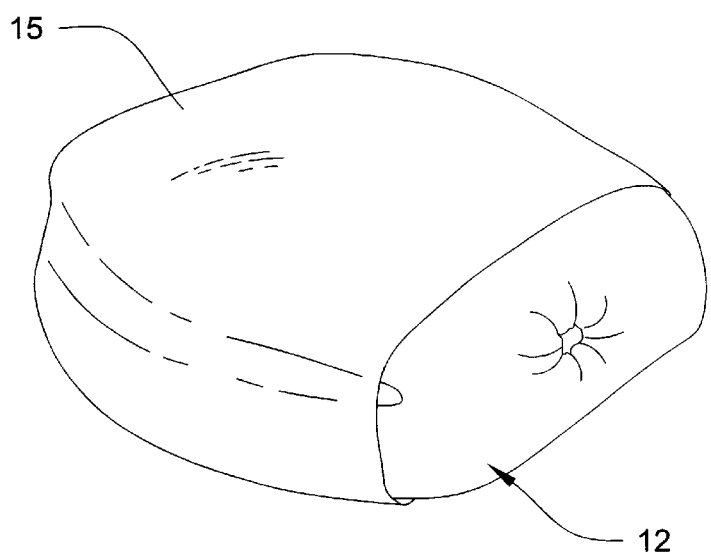
FIG. 7 is a perspective view of the combination tampon/panty shield fully inserted into the disposal pouch.

FIGS. 1–7 show various aspects of an exemplary embodiment of the combination tampon/panty shield of the present invention generally designated 10. Combination tampon/panty shield 10 includes a panty shield portion, generally designated 12; a tampon, generally designated 14; and a disposal pouch 15.

Panty shield portion 12 includes a moisture proof outer layer 16 provided with two exterior pockets 18,20, and a centrally located finger insertion cavity 22 that extends inward through an in inner absorbent layer 24 of panty shield portion 12 that is adhesively bonded to a backside surface 26 of the moisture proof outer layer 16.

Tampon 14 extends outwardly from inner absorbent layer 24 and has a portion 30 of finger insertion cavity 22 extending into a bottom tampon portion 34 thereof.

In use, the two exterior pockets 18,20, and the centrally located finger insertion cavity 22 are used during insertion and/or removal of the tampon into or out of the vagina.

It can be seen from the preceding description that a combination tampon/panty shield has been provided.

It is noted that the embodiment of the combination tampon/panty shield described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A combination tampon/panty shield comprising:
   a panty shield portion including a moisture proof outer layer provided with two exterior finger receiving pockets and a centrally located finger insertion cavity extending inward through an inner absorbent layer adhesively bonded to a backside of the moisture proof outer layer and having a portion of the finger insertion cavity extending into a bottom tampon portion that extends outwardly from the inner absorbent layer
   the two exterior finger receiving pockets and the finger insertion cavity being used during insertion and/or removal of the tampon into or out of the vagina;

the moisture proof outer layer further having a disposal pouch pocket on one end thereof with a pouch opening facing toward the opposite end of the panty shield portion;

the disposal pouch pocket being invertable about its own end to cover both ends of the panty shield portion when the panty shield portion is folded in half with the inner absorbent layer in contact with itself and the bottom tampon portion between two sections of the inner absorbent layer.

* * * * *